US008993762B2

(12) United States Patent
Huang et al.

(10) Patent No.: US 8,993,762 B2
(45) Date of Patent: Mar. 31, 2015

(54) TOTAL SYNTHESIS OF THAXTOMIN A ANALOGUES AND THEIR INTERMEDIATES

(71) Applicant: Marrone Bio Innovations, Inc, Davis, CA (US)

(72) Inventors: Huazhang Huang, Woodland, CA (US); Dong Yan, Tianjin (CN); Zhijie Xue, Tianjin (CN); Hongbo Zhang, Tianjin (CN)

(73) Assignee: Marrone Bio Innovations, Inc., Davis, CA (US)

( * ) Notice: Subject to any disclaimer, the term of this patent is extended or adjusted under 35 U.S.C. 154(b) by 0 days.

(21) Appl. No.: 13/840,975

(22) Filed: Mar. 15, 2013

(65) Prior Publication Data
US 2014/0275541 A1    Sep. 18, 2014

(51) Int. Cl.
C07D 403/06    (2006.01)

(52) U.S. Cl.
CPC .................................... *C07D 403/06* (2013.01)
USPC .......................................................... 544/373

(58) Field of Classification Search
CPC .................................................... C07D 403/06
See application file for complete search history.

(56) References Cited

U.S. PATENT DOCUMENTS

| | | | |
|---|---|---|---|
| 4,309,208 A | 1/1982 | Takematsu et al. | |
| 4,990,178 A | 2/1991 | Haneishi et al. | |
| 6,756,341 B2 | 6/2004 | Grimm | |
| 7,393,812 B2 | 7/2008 | Gerwick, III et al. | |
| 7,504,244 B2 | 3/2009 | Szabo et al. | |
| 7,989,393 B2 | 8/2011 | Kang et al. | |
| 8,476,195 B2 | 7/2013 | Koivunen et al. | |
| 2004/0192551 A1 | 9/2004 | Bessette | |
| 2009/0099022 A1 | 4/2009 | Fernandez et al. | |
| 2009/0156553 A1 | 6/2009 | Hupe et al. | |
| 2010/0152047 A1 | 6/2010 | Hupe et al. | |
| 2010/0173777 A1 | 7/2010 | Hupe et al. | |
| 2010/0267560 A1 | 10/2010 | Leep et al. | |
| 2013/0190175 A1 | 7/2013 | Koivunen et al. | |
| 2013/0217573 A1 | 8/2013 | Koivunen et al. | |
| 2013/0288896 A1 | 10/2013 | Koivunen et al. | |
| 2013/0296169 A1 | 11/2013 | Koivunen et al. | |

FOREIGN PATENT DOCUMENTS

| | | |
|---|---|---|
| WO | WO 2008124675 | 10/2008 |
| WO | WO 2013066894 | 10/2008 |
| WO | WO 2010006677 | 6/2010 |
| WO | WO 2010066677 | 6/2010 |
| WO | WO 2010078452 | 7/2010 |
| WO | WO 2014013343 | 1/2014 |

OTHER PUBLICATIONS

Zhang, H., et al. "Total Synthesis of Thaxtomin A and Its Stereoisomers and Findings of Their Biological Activities." Org. Letters. (2013), vol. 15, No. 22, pp. 5670-5673.*

Beausejour, "Production of Thaxtomin A by *Streptomyces scabies* Strains in Plant Extract Containing Media," *Can. J. Microbiol.* 45:764-768 (1999).

Duke, "Natural Products as Sources of Herbicides: Current Status and Future Trends," *Weed Res.* 40:99-111 (2000).

Duke, "United States Department of Agriculture-Agricultural Research Service Research on Natural Products for Pest Management," *Pest Management Sci.* 59:708-717 (2003).

Duval, "Thaxtomin A Induces Programmed Cell Death in *Arabidopsis thaliana* Suspension-Cultured Cells," *Planta* 222:820-831 (2006).

Fry, "Thaxtomin A: Evidence for a Plant Cell Wall Target," *Physiolog. Molec. Plant Pathol.* 60:1-8 (2002).

Gelin, "Synthetic Studies on Thaxtomins A and B, Phytotoxins Associated with *Streptomyces scabies*, the Causal Organism of the Potato Common Scab," *J. Org. Chem.* 58(13): 3473-3475 (1993).

Healy, "The txtAB Genes of the Plant Pathogen *Streptomyces acidiscabies* Encode a Peptide Synthetase Required for Phytotoxin Thaxtomin A Production and Pathogenicity," *Molec. Microbiol.* 38:794-804 (2000).

Hiltunen, "Influence of Thaxtomins in Different Combinations and Concentrations on Growth of Micropropagated Potato Shoot Cultures," *J. Agric. Food Chem.* 54:3372-3379 (2006).

Hoagland, "Microbial Allelochemicals and Pathogens as Bioherbicidal Agents," *Weed Technol.* 15:835-857 (2001).

Johnson, "Plant-Pathogenic *Streptomyces* Species Produce Nitric Oxide Synthase-Derived Nitric Acid in Response to Host Signals," *Chemistry & Biology* 15:43-50 (2007).

King, "Isolation and Characterization of Phytotoxins Associated with *Streptomyces scabies*," *J. Chem. Soc. Chem. Commun.* 13:849-850 (1989).

King, "Chemistry of Phytotoxins Associated with *Streptomyces scabies*, the Causal Organism of Potato Common Scab," *J. Agric. Food Chem.* 40:834-837 (1992).

King, "Synthesis of Thaxtomin C," *Can. J. Chem* 75:1172-1173 (1997).

King, "Herbicidal Properties of the Thaxtomin Group of Phytotoxins," *J. Agric. Food Chem.* 49:2298-2301 (2001).

King, "More Chemistry of the Thaxtomin Phytotoxins," *Phytochemistry* 64:1091-1096 (2003).

King, "The Thaxtomin Phytotoxins: Sources, Synthesis, Biosynthesis, Biotransformation and Biological Activity," *Phytochemistry* 70:833-841 (2009).

Koivunen, "Evaluation of a New Natural Product Herbicide for Rice Weed Control," *Proceedings of the California Weed Science Society* 61:113 (2009).

(Continued)

*Primary Examiner* — Andrew D Kosar
*Assistant Examiner* — John S Kenyon
(74) *Attorney, Agent, or Firm* — Ying-Horng Liu

(57) ABSTRACT

Improved synthetic methods for the production of thaxtomin analogs, particularly thaxtomin A, and intermediates therefore such as substituted tryptophans and in particular, 4-nitro-L-tryptophan, and substituted phenyl acrylic acids are disclosed. Bioassays show that the synthetic thaxtomin A is not significantly different from the natural one in herbicidal activity.

8 Claims, 1 Drawing Sheet

(56) References Cited

OTHER PUBLICATIONS

Loria, "Differential Production of Thaxtomins by Pathogenic *Streptomyces* Species in Vitro," *Phytopathology* 85:537-541 (1995).
Molesworth, "Snythesis and Phytotoxicity of Structural Analogues of Thaxtomin Natural Products," *Aust. J. Chem* 63:813-820 (2010).
Scheible, "An Arabidopsis Mutant Resistant to Thaxtomin A, a Cellulose Synthesis Inhibitor from *Streptomyces* Species," *The Plant Cell* 15:1781-1794 (2003).
Taylor, "Casoron, a New Aquatic Herbicide," *Hyacinth Control Journal/J. of Aquatic Plant Management* 5:20-21 (1966), available at www.apms.org/japm/vol05/v5p20.pdf.
Examination Report for NZ App. No. 596336 dated Aug. 23, 2012.
Examination Report for NZ App. No. 593916 dated May 4, 2012.
Extended Search Report for EP App. No. 098371743 dated May 12, 2012.
Extended Search Report for EP App. No. 10765219.0 dated Jul. 23, 2012.
International Search Report and Written Opinion for PCT App No. PCT/US2009/069856 dated Aug. 13, 2010.
International Search Report and Written Opinion for PCT App. No. PCT/US2010/031317 dated Nov. 11, 2010.
International Preliminary Report on Patentability for PCT App. No. PCT/US2010/031317 dated Oct. 18, 2011.
International Search Report and Written Opinion for PCT App. No. PCT/IB2013/002214 dated Jan. 28, 2014.
Office Action (Final Rejection) for U.S. Appl. No. 12/761,382 (Dec. 22, 2011).
Office Action (Non-Final Rejection) for U.S. Appl. No. 12/761,382 (Oct. 5, 2012).
Office Action (Final Rejection) for U.S. Appl. No. 12/650,315 (Jan. 19, 2012).
Office Action (Non-Final Rejection) for U.S. Appl. No. 12/650,315 (Sep. 27, 2012).
International Search Report and Written Opinion for PCT App No. PCT/US2014/011885 dated May 30, 2014.

\* cited by examiner

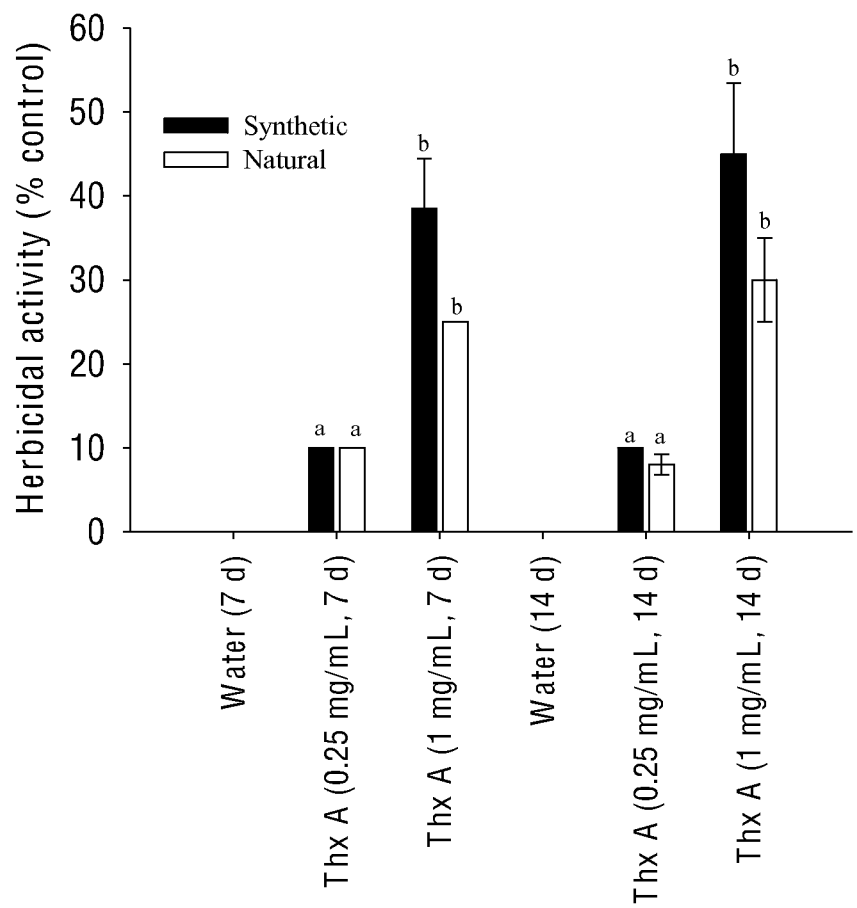

TOTAL SYNTHESIS OF THAXTOMIN A ANALOGUES AND THEIR INTERMEDIATES

FIELD

Provided is a method of synthesis for thaxtomin analogues and their intermediates. In particular the invention is in a method of total syntheses of thaxtomin A, its analogues and intermediates therefore including 4-nitro-L-tryptophan and (Z)-2-hydroxy-3-(3-hydroxyphenyl)acrylic acid.

BACKGROUND

Phytotoxins produced by *Streptomyces scabies* were suspected as the causal agent of potato scab in 1926 [Fellow H., 1926; King et al. 2009]. The phytotoxins were isolated from *S. scabies* on immature potato tubers. In 1989 the phytotoxins were found to contain a class of compounds containing 4-nitro-L-tryptophan and phenylalanine linked in an L,L-configured cyclodipeptide, named as thaxtomins [King et al., 1989]. Thaxtomin A is the major metabolite from *S. scabies*. Subsequently, thaxtomins were also found from other *Streptomyces* species such as *S. acidiscabies, S. turgidiscabies, S. europaeiscabiei, S. niveiscabiei* and *S. ipomoeae* [King et al., 1994 and 2009]. Over 11 analogs of thaxtomins have been purified from these microorganisms.

Thaxtomin A has been found to cause hypertrophy of plant cells at nanomolar amounts and cell death at concentrations similar to those found in scab lesions on field infected potato tubers [Lawrence et al., 1990]. Structural-activity relationship (SAR) studies revealed that the presence of the nitro group at 4-position of indole ring of the tryptophan moiety and an L,L-configuration of the diketopiperazine ring are specific for phytotoxicity [King et al., 1989 & 1992]. Other studies relating to mode of action have suggested that thaxtomins may, like dichlobenil and isoxaben, inhibit the synthesis of cellulose [King et al., 2001, Schneegurt et al., 1994; Scheible et al., 2003]. Consequently, thaxtomins have been investigated as herbicides. U.S. Pat. No. 7,989,393 to Kang et. al. discloses methods for treating or controlling algae using one or more thaxtomins. U.S. Patent Publication 2010/0167930 A1 shows a process using thaxtomin and thaxtomin containing compositions for controlling the germination and growth of weeds in cereal, turf, timothy grass and pasture grass cultures. WO 2010/121079 A2 shows the use of thaxtomin for controlling the germination and growth of broadleaf, algae, sedge and grass weeds, particularly in rice growing systems and/or aquatic based weeds.

During identification and verification of the structure of thaxtomin A, 4-nitrotryptophan was identified as the precise moiety of the structure of thaxtomin A [King et al., 1992]. Subsequently, 4-nitrotryptophan and N-acetyltryptophan were proposed as possible intermediates for thaxtomin A biosynthesis [King et al., 1995; King et al., 2003]. Ultimately, it was verified that 4-nitrotryptophan is a substrate for the non-ribosomal peptide synthetase TxTB in the thaxtomin A biosynthetic pathway [Johnson et al., 2009]. The addition of 4-nitrotryptophan in fermentation broth has been shown to enhance the yield of thaxtomin A [Johnson et al., 2009].

Due to difficulties of enhancing the yield of thaxtomin A through wild strains of *Streptomyces* species, it is crucial to feed these microorganisms with 4-nitrotryptophan during fermentation. However, this compound is not commercially available. The synthesis of 4-nitrotryptophan has been reported in numerous publications. For example, 4-nitrotryptophan was prepared by tryptophan nitration with nitric acid and acetic acid [King et al., 1992 & 1995] and synthesis of 4-nitrotryptophan derivatives from nitrogramines was also reported [King et al., 2009]. However, there were some shortcomings for such reported synthesis routes. For example, nitration with nitric acid and acetic acid is not selective and results in the formation of numerous reaction products requiring separation procedures. In addition, the 4-nitrotryptophan in thaxtomin A should be in the L configuration, not a D,L racemic mixture synthesized from nitrogramines. Although racemic 4-nitro-D,L-tryptophan also could enhance the yield of thaxtomin A, it is still questionable whether the microorganisms can utilize the 4-nitro-D-tryptophan optical isomer. Therefore, it is important to obtain a reliable synthetic method to synthesize 4-nitro-L-tryptophan.

Thaxtomin produced by fermentation is relatively expensive in comparison to those other herbicides having a similar mode of action but which can be produced by synthetic methods. This is in part because of low yields in the fermentation processes. It is desirable to use a synthetic approach to obtain this compound. A number of methods have been reported in the literature for the synthesis of thaxtomins. The earliest reported method synthesizes thaxtomin A analog without the nitro group on the 4 position of tryptophan in a racemic synthesis starting with 1,4-diacetyl 2,5-piperazinedione [Gelin et al., 1993]. That five step method results in a total yield of about 6.3%. The second reported method shows the synthesis of thaxtomin C in two steps, beginning with the condensation of N-methyl-L-4-nitrotryptophan methyl ester and t-Boc-L-phenylalanine to give a dipeptide methyl ester which is then cyclized to form the thaxtomin analogue [King 1997]. The third method starting from fermented thaxtomin A synthesizes thaxtomin A alkyl ethers for an SAR study [Krasnoff et al., 2005]. The last reported method shows the synthesis of thaxtomin C and thaxtomin D analogues with a 2,5-diketopiperazine core and L-phenylalanine with an apparent racemization in the described procedure [Molesworth et al., 2010]. Molesworth's approach built upon the piperazinedione core of glycine anhydride and the use of aldol condensation chemistry. Additionally, the patent literature shows synthetic methods which use 2,5-diketopiperazine as a core to produce compounds with herbicidal properties. For example, each of U.S. Patent Publication No. 2010/0152047 A1, and each of EP 2 054 394 B1 (U.S. 2010/0173777 A1) and EP 1 971 581 B1 (U.S. 2009/0137396 A1) propose 2,5-diketopiperine derivatives as herbicides. Clearly, an efficient synthetic approach for thaxtomins such as thaxtomin A with proper stereo specificity and intermediates therefore is necessary to provide sufficient quantities for herbicidal uses.

SUMMARY

Provided are improved synthetic methods for the production of thaxtomin analogues, particularly thaxtomin A, and intermediates therefore such as substituted tryptophans and in particular, 4-nitro-L-tryptophan, and substituted phenyl acrylic acids. Bioassays show that there is no significant difference in herbicidal activity between synthesized thaxtomin A and thaxtomin A obtained from natural sources.

In particular, provided is a method for the preparation of a thaxtomin analog having the structure (I)

Wherein R1 and R2 are each is one or more of lower alkyls (such as methyl), hydroxyl, halogen, fluoromethyl difluoromethyl, trifluoromethyl, nitro, or any other groups such as amines, methoxy, fluoromethoxy, difluoromethoxy, and trifloromethoxy. In a particular embodiment, each benzene ring may have multiple R1 or R2 substuents The method comprises the steps of:

(a) providing a tryptophan amide or analog thereof analog (b) providing a substituted or unsubstituted phenyl acrylic acid (c) Reacting said tryptophan amide of (a) with said phenyl acrylic acid of (b) to obtain a compound having the structure (A)

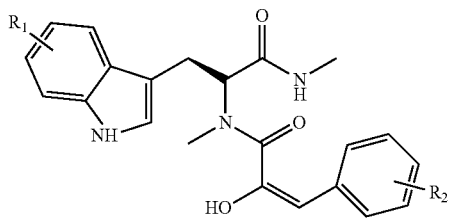

Wherein $R_1$ and $R_2$ each are one or more of lower alkyl (such as methyl), hydroxyl, halogen, fluoromethyl difluoromethyl, trifluoromethyl, nitro, or any other groups such as amines methoxy, fluoromethoxy, difluoromethoxy, and trifloromethoxy and (d) subjecting the compound having the structure (A) to a cyclization agent to obtain the structure (I).

In a particular embodiment the thaxtomin analog is a thaxtomin A analog.

BRIEF DESCRIPTION OF THE FIGURES

FIG. 1 shows a comparison of herbicidal activity between synthesized and natural thaxtomin A against 15 day mustard plants.

DESCRIPTION OF SPECIFIC EMBODIMENTS

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a," "and" and "the" include plural references unless the context clearly dictates otherwise.

As noted above, provided is a method for the synthesis of a thaxtomin analog. In a particular embodiment, the thaxtomin analog is a thaxtomin A analog. In a most particular embodiment, the thaxtomin is Thaxtomin A. In particular, the method comprises reacting a tryptophan amide analog with a phenylacrylic acid analog and subsequent cyclizing the resulting product. In particular, the tryptophan amide analog has the structure (I)

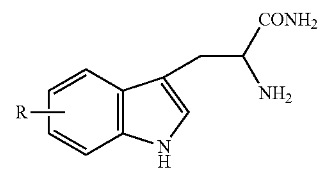

wherein R is lower alkyl (such as methyl), hydroxyl, halogen, fluoromethyl difluoromethyl, trifluoromethyl, nitro, or any other groups such as but not limited to amines methoxy, fluoromethoxy, difluoromethoxy, and trifloromethoxy.

In a more particular embodiment, the tryptophan amide analog has the structure (I)

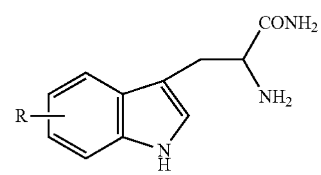

wherein R is $NO_2$.

R may be in multiple locations on the benzene ring. [

In an even more particular embodiment, the tryptophan amide analog is TA-107 set forth below.

TA-107

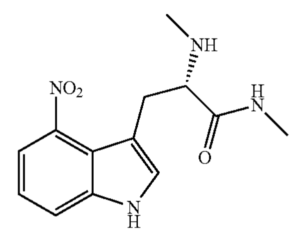

The substituted phenylacrylic acid used in the method set forth herein may have the structure (2)

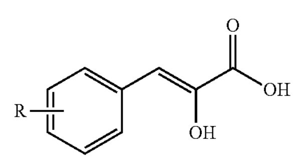

wherein R is lower alkyl (such as methyl), hydroxyl, halogen, fluoromethyl difluoromethyl, trifluoromethyl, nitro, or any other groups such as but not limited to amines methoxy, fluoromethoxy, difluoromethoxy, and trifloromethoxy or its keto tautomer In a more particular embodiment, R is OH. In an even more particular embodiment, the substituted phenylacrylic acid has the structure TA-205.

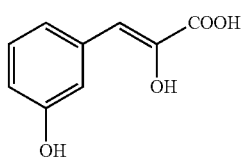 [SMILES: O=C(O)/C(O)=C/c1cccc(O)c1]

or its keto tautomer (TA-205a)

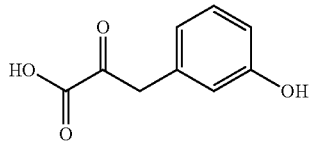 [SMILES: O=C(O)C(=O)Cc1cccc(O)c1]

The keto/enol tautomer may be separated using methods known in the art, e.g., liquid chromatography.
The product obtained has the structure

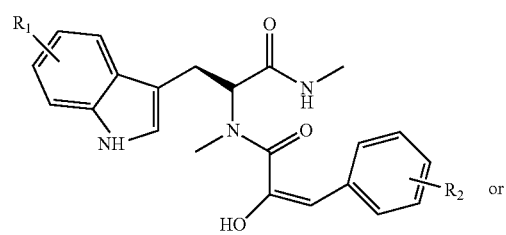

(A1)

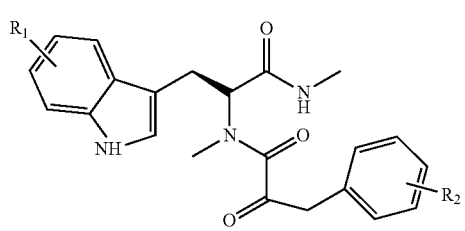

(A2)

wherein R1 and R2 are each lower alkyl (such as methyl), hydroxyl, halogen, fluoromethyl difluoromethyl, trifluoromethyl, nitro, or any other groups such as but not limited to amines methoxy, fluoromethoxy, difluoromethoxy, and trifloromethoxy. In a particular embodiment the product obtained is TA-108 described herein.

The compound (A) may be cyclized with a cyclization agent. In a particular embodiment, the cyclization is by means of an organic base. In a particular embodiment, the organic base is potassium hydroxide. In another particular embodiment, the organic base has substituted groups. In another particular embodiment, the organic base is a chiral Lewis base. The organic base may also be selected from the group consisting of substituted or unsubstituted pyridine, amine, imidazole, benzimidazole, histidine, and phosphazene.

EXAMPLES

Provided herein is an exemplification of a preferred embodiment by means of a series of steps for the synthesis of 4-nitro-L-tryptophan, 2-hydroxy-phenyl acrylic acid and the synthesis of thaxtomin A. The steps include providing certain compounds which may be a starting material, the product of a reaction or resulting from the converting or conversion of one compound to another or to a different form of the compound. Included are two pathways for the total synthesis of 4-nitro-L-tryptophan shown schematically in the following disclosure.

1. Synthesis of 4-nitro-L tryptophan

The 4-nitro-L-tryptophan is designated as TA-TM-1. The first synthetic pathway may be summarized schematically as follows:

SCHEME 1

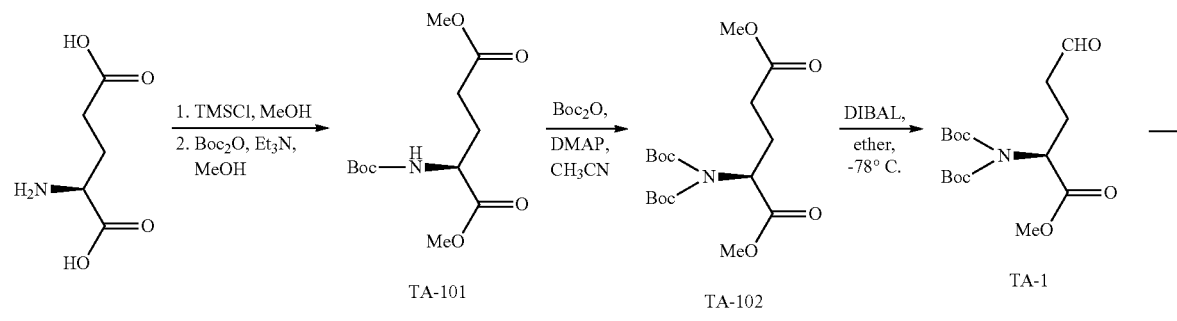

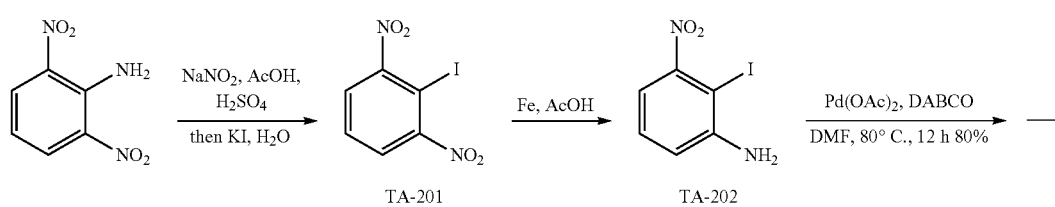

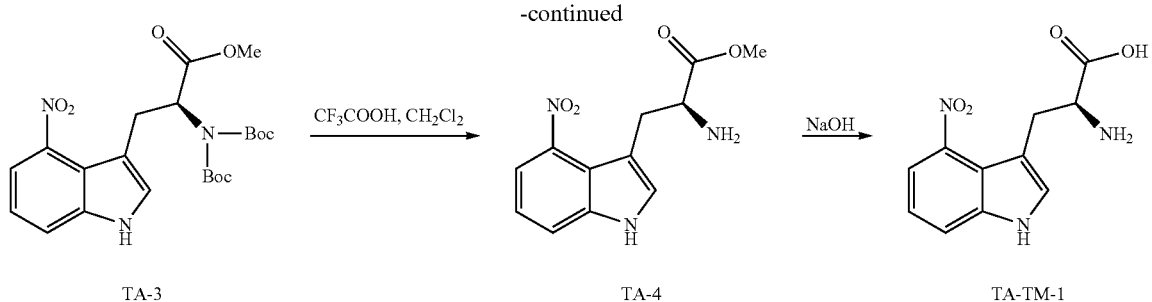

The second synthetic pathway may be summarized as follows

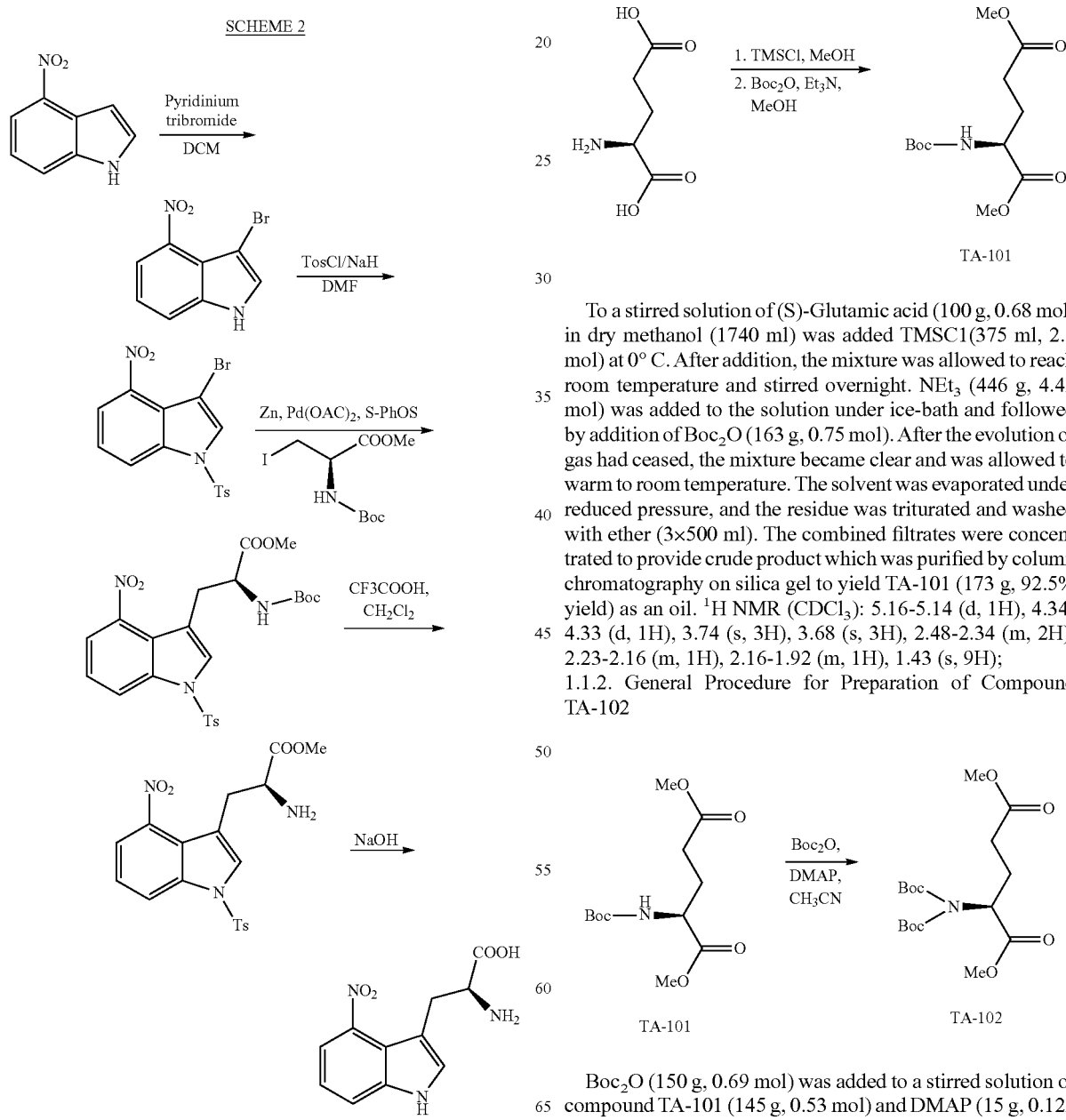

1.1.1. General Procedure for Preparation of Compound TA-101

To a stirred solution of (S)-Glutamic acid (100 g, 0.68 mol) in dry methanol (1740 ml) was added TMSC1 (375 ml, 2.9 mol) at 0° C. After addition, the mixture was allowed to reach room temperature and stirred overnight. NEt$_3$ (446 g, 4.42 mol) was added to the solution under ice-bath and followed by addition of Boc$_2$O (163 g, 0.75 mol). After the evolution of gas had ceased, the mixture became clear and was allowed to warm to room temperature. The solvent was evaporated under reduced pressure, and the residue was triturated and washed with ether (3×500 ml). The combined filtrates were concentrated to provide crude product which was purified by column chromatography on silica gel to yield TA-101 (173 g, 92.5% yield) as an oil. $^1$H NMR (CDCl$_3$): 5.16-5.14 (d, 1H), 4.34-4.33 (d, 1H), 3.74 (s, 3H), 3.68 (s, 3H), 2.48-2.34 (m, 2H), 2.23-2.16 (m, 1H), 2.16-1.92 (m, 1H), 1.43 (s, 9H);

1.1.2. General Procedure for Preparation of Compound TA-102

Boc$_2$O (150 g, 0.69 mol) was added to a stirred solution of compound TA-101 (145 g, 0.53 mol) and DMAP (15 g, 0.122 mol) in dry CH$_3$CN (1600 mL) at room temperature. The reaction became slightly red with gas evolution. The mixture was stirred for 2 h, and TLC (v/v, PE:EA=3:1) showed remaining starting material (TA-101). A further amount of Boc₂O (75 g, 0.35 mol) was then added and the mixture was additionally stirred overnight. The solvent was evaporated under reduced pressure, and the crude product was purified by column chromatography on silica gel to yield TA-102 (176 g, 89% yield) as an oil.

1.1.3. General Procedure for Preparation of Compound TA-1

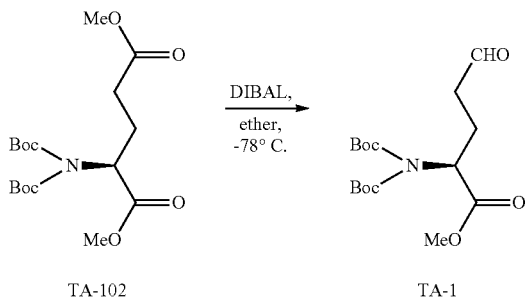

To a stirred solution of compound TA-102 (87 g, 0.23 mol) in dry ether (1800 ml) was added dropwise DIBAL (570 ml, 0.57 mol) at −78° C. The reaction was quenched with water (38 ml) as TLC showed disappearance of the starting material. The mixture was dried over Na₂SO₄, filtered and concentrated to give crude TA-1 (71.6 g, 89% yield), which was directly used in the next step without further purification. $^1$H NMR (CDCl₃): 9.79 (s, 1H), 4.92-4.89 (m, 1H), 3.74 (s, 3H), 2.65-2.47 (m, 3H), 2.21-2.16 (m, 1H), 1.54 (s, 18H)

1.1.4. General Procedure for Preparation of Compound TA-201

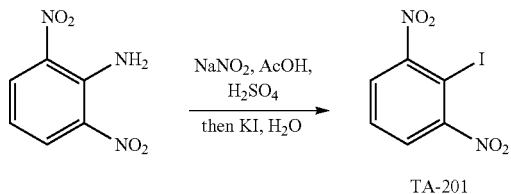

Sodium nitrite (22 g, 0.31 mol) was added portion-wise to sulfuric acid (225 ml) and heated at 70° C. until the solution became clear. The resulting solution was cooled to 40° C. and 2,6-dinitroaniline (50 g, 0.27 mol) dissolved in AcOH (550 ml) was added dropwise while the temperature was maintained below 40° C. The reaction was continued for an additional 0.5 h. The reaction mixture then was poured into a stirred solution of KI (50 g, 0.31 mol) in water at 70° C. The resulting solution was stirred for 15 minutes and then poured into 3000 ml of water. The solid was filtered, washed with water and dried to give 40 g (yield 50.6%). The crude solid was used without further purification 1.1.5. General Procedure for Preparation of Compound TA-202

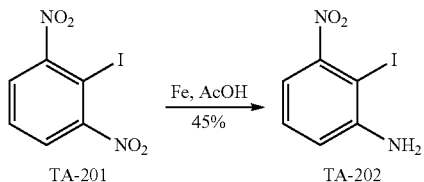

To a solution of compound TA-201 (70 g, 0.238 mol) in 700 ml AcOH, Fe powder (40 g, 0.714 mol) was added portion-wise at 110° C. When the addition was complete, the mixture was stirred for 0.5 h at 110° C. When TLC (v/v, PE:EA=4:1) showed that the starting material (TA-201) had disappeared, the mixture was cooled to room temperature. Filtered, the solid was washed by CH₂Cl₂ (500 ml), the organic layers combined and poured into 2000 ml water, CH₂Cl₂ (3×1000 ml) extracted, the organic layer was sequentially washed by saturated NaHCO₃ and brine. The solvent was concentrated under vacuum to yield the crude which was purified by silica gel chromatography to give 27 g (yield 43%) of TA-202.

1.1.6. General Procedure for Preparation of Compound TA-3

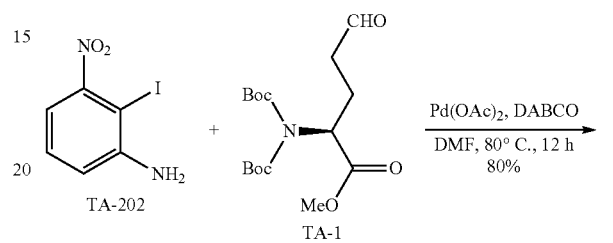

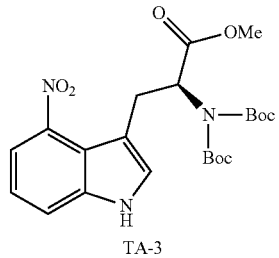

A mixture of TA-202 (30 g, 0.113 mol), TA-1 (30 g, 0.087 mol) and DABCO (39 g, 1.3 mol) in DMF (300 ml) was degassed by argon for 20 min, and then Pd(OAc)₂ (1.5 g, 6.7 mmol) was added. The mixture was warmed to 80° C. and stirred for 10 h in an argon atmosphere. After the reaction mixture was cooled to room temperature, EA (500 ml) was added. The mixture was sequentially washed with water (1000 ml) and brine. The organic solvent was concentrated in vacuum to give crude which was purified by column chromatography on silica gel to afford 12 g (yield 22%) TA-3.

1.1.7. General Procedure for Preparation of Compound TA-4

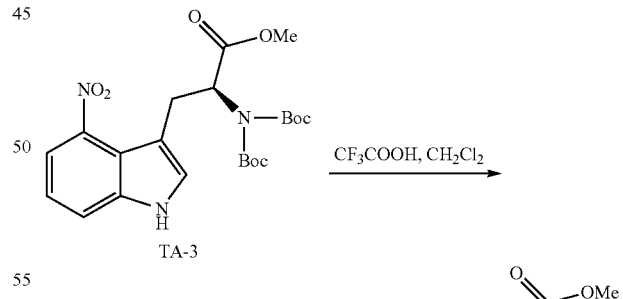

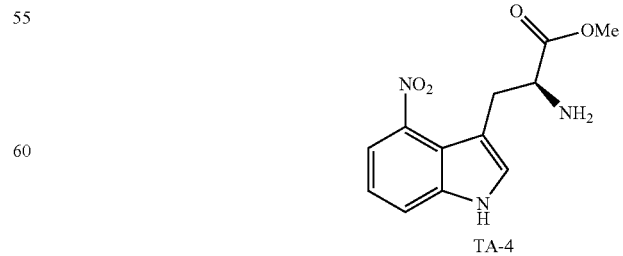

CF₃COOH (200 ml) was added dropwise with gas evolution to a solution of TA-3 (45 g, 0.097 mol) in CH₂Cl₂ (400 ml). The reaction mixture was stirred overnight and concentrated the solvent in vacuum to give a crude oil which used for the next step without further purification.

1.1.8 General Procedure for Preparation of Compound TA-TM-1

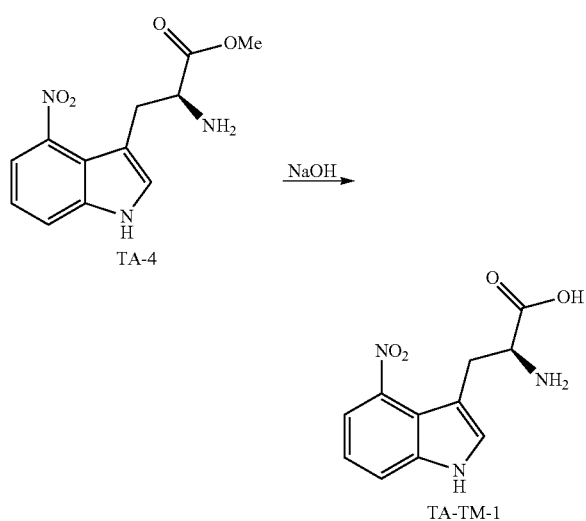

The crude TA-4 from the prior step was dissolved in water/EtOH (400 mL, v/v, 1:1). A 10% aqueous NaOH solution was added dropwise to TA-4 solution under ice-bath conditions to adjust to pH 8, and then additional 10% aqueous NaOH (100 ml, 0.25 mol) was added to the solution. After the mixture was stirred for 2 h, TLC (v/v, DCM:MeOH=15:1) showed the starting material had disappeared. 2N HCl aqueous solution was added to adjust the solution to pH 6. The mixture was stirred for another 2 h and filtered. The recovered solid was washed with water (100 ml) and EtOH (100 ml) and dried in infrared light for 4 h to give 16 g TA-TM-1 (two step total yield: 66%). $^1$H NMR (D$_2$O) δ: 7.76-7.74 (d, 1H), 7.68-7.67 (d, 1H), 7.32 (s, 1H), 7.14-7.10 (t, 1H), 3.19-3.16 (t, 1H), 3.08-3.02 (m, 1H), 2.93-2.88 (m, 1H).

The second pathway for synthesis of 4-nitro-L-tryptophan TA-104 will be described as part of the description of the synthesis of thaxtomin A.

2. Synthesis of Thaxtomin A

Although a few methods have been published for synthesis of thaxtomin A analogs, a total synthesis of thaxtomin A, which is the most active ingredient, has not been disclosed. The technical bottle neck of thaxtomin A synthesis is the tertiary alcohol in the middle ring because this hydroxyl is chiral and its presence and configuration were demonstrated to be correlated directly with its bioactivity, therefore, an important aspect of the invention is from TA-107 to Thaxtomin A described in the following, especially cyclization to form the middle ring under basic conditions. In the current method described here as an example, potassium hydroxide was used, resulting in an equal quantity of a mixture of two diastereomers (i.e., 50:50). In the case example, both enantiomers were obtained in high enantiomeric purity by preparative chiral liquid chromatography. In the meanwhile, different organic base were optimized for the selective synthesis of the active target.

The synthetic route is schematically depicted as follows

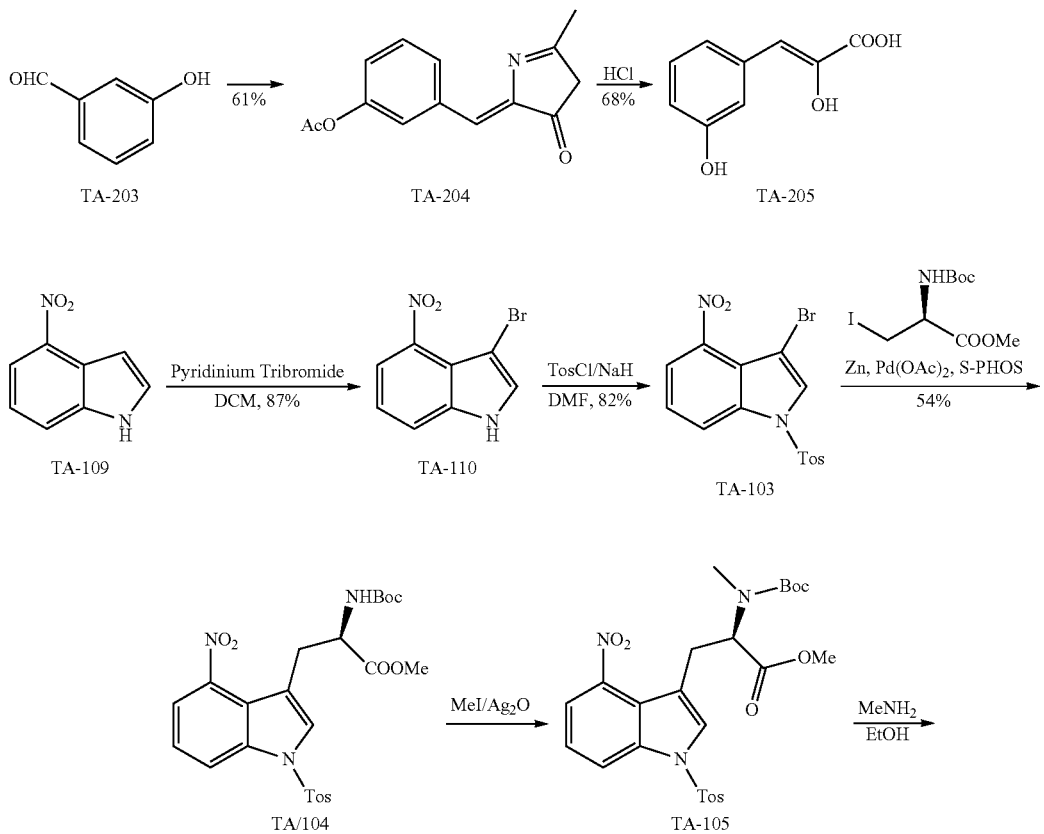

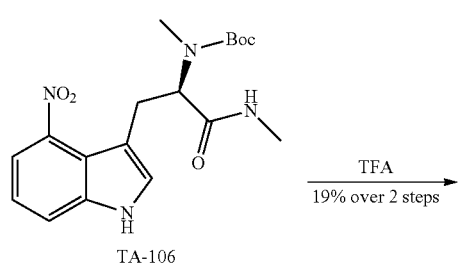

TA-106

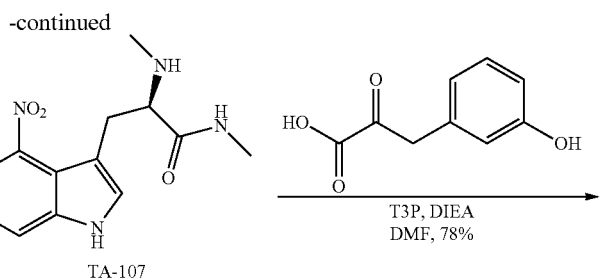

TA-107

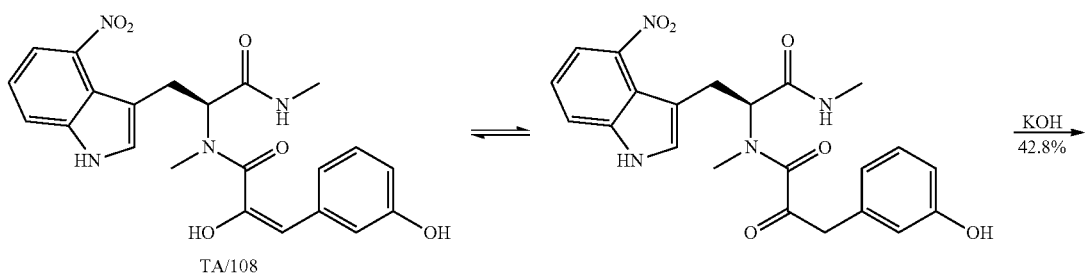

TA/108

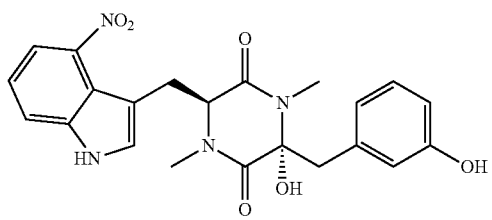

Thaxtomin A 2.1. General Procedure for Preparation of Compound TA-204

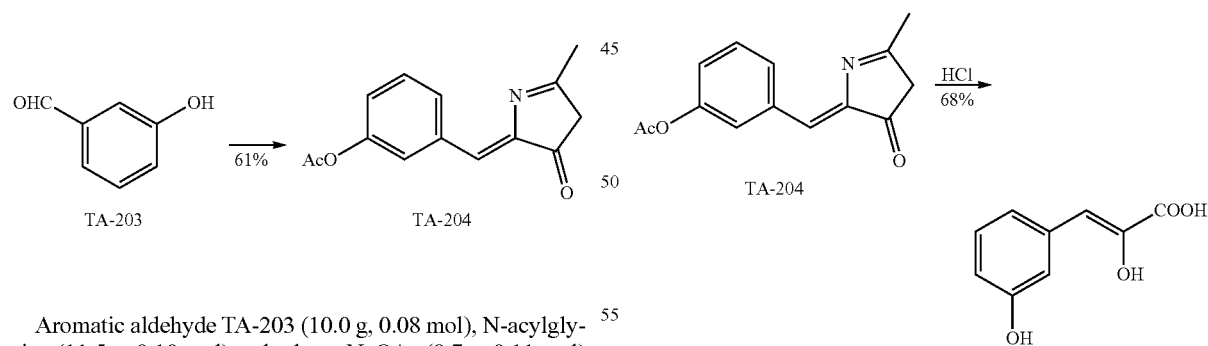

Aromatic aldehyde TA-203 (10.0 g, 0.08 mol), N-acylglycine (11.5 g, 0.10 mol), anhydrous NaOAc (8.7 g, 0.11 mol) and Ac$_2$O (42.0 g, 0.41 mol) were mixed and stirred at 120° C. for 5 hours. After completion of the reaction, the mixture was allowed to cool to room temperature. Then ice water was added. The resulting yellow precipitate was filtered, washed with 50% aqueous EtOH (20 mL), dried under vacuum and was recrystallized from acetone (50 mL) to give slightly yellow crystals of TA-204 (10.1 g, 61% yield). $^1$H NMR (400 MHz, CDCl$_3$) δ 7.93 (s, 1H) 7.85 (d, J=8.0 Hz, 1H), 7.45 (t, J=8.0 Hz, 1H), 7.17 (dd, J=8.0, 1.6 Hz, 1H), 7.10 (s, 1H), 2.42 (s, 3H), 2.34 (s, 3H);

2.2. General Procedure for Preparation of Compound TA-205

A mixture of TA-204 (10 g, 0.04 mol) in 3N HCl 200 mL was refluxed at 100° C. for 4 h. Subsequently, the resulting mixture was allowed to cool to room temperature and the resulting precipitate was collected by filtration. The filtrate was extracted with EtOAc. The organic extract was evaporated to give a residue which was combined with the filtered precipitate. The total product was dried under vacuum and crystallized from 50% aqueous EtOH (30 mL) to afford TA-205 (5.0 g, 68% yield) as slightly yellow crystals which can be used directly in the following steps.

2.3. General Procedure for Preparation of Compound TA-110

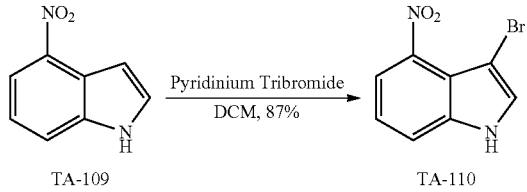

To a solution of TA-109 (11.0 g, 0.06 mol) in pyridine (60 mL) was added dropwise pyridinium hydrobromide perbromide (20.0 g, 0.06 mol) in pyridine (20 mL) at 0° C. After being stirred for 0.5 h at 0° C., the reaction mixture was poured into Et$_2$O and the precipitate was removed by filtration. The filtrate was washed successively with 1N aqueous sodium hydroxide (50 mL), water (50 mL), and brine (20 mL) and concentrated. The residue was purified by column chromatography using hexane and increasing amounts of EtOAc to give TA-110 (16.3 g, 87% yield). $^1$H NMR (400 MHz, CDCl$_3$) δ 12.35 (s, 1H) 7.90 (s, 1H), 7.82 (d, J=8.4 Hz, 1H), 7.74 (d, J=7.2 Hz, 1H), 7.30 (t, J=8.0 Hz, 1H);

2.4. General Procedure for Preparation of Compound TA-103

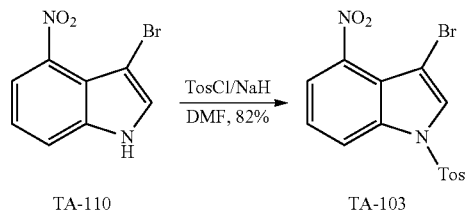

NaH in oil (2.6 g, 0.06 mol) was washed with hexane and suspended in dry DMF (50 mL) under an Argon atmosphere. To this suspension was added TA-110 (14.2 g, 0.06 mol) in dry DMF (20 mL) at 0° C. After the mixture was stirred for 10 min, tosyl chloride (12.3 g, 0.06 mol) was added and the reaction mixture was stirred at 0° C. for 2 h. The mixture was poured into H$_2$O and extracted with EtOAc. The EtOAc layer was washed with brine, dried over Na$_2$SO$_4$, and concentrated. The residue was purified by column chromatography using hexane and increasing amounts of EtOAc to give TA-103 (23.3 g, 82%). $^1$H NMR (400 MHz, CDCl$_3$) δ 8.27 (d, J=8.4 Hz, 1H), 7.84 (s, 1H), 7.78 (d, J=8.4 Hz, 2H), 7.74 (d, J=7.6 Hz, 1H), 7.44 (t, J=7.6 Hz, 1H), 7.29 (d, J=8.4 Hz, 2H), 2.39 (s, 3H).

2.5. General Procedure for Preparation of Compound TA-104

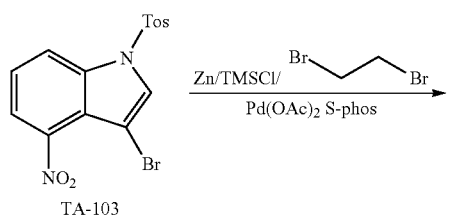

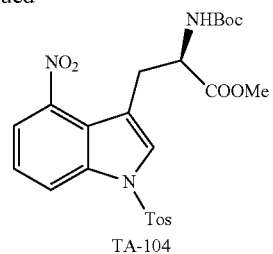

1,2-Dibromoethane (4.37 g, 0.02 mol) was added to a stirred suspension of zinc dust (37.80 g, 0.58 mol) in DMF (50 mL), and the mixture was stirred at 50° C. for 30 min. The reaction mixture was allowed to cool to room temperature. Chlorotrimethylsilane (0.50 g, 4.60 mmol) was added to the mixture, and the mixture was stirred for a further 30 min vigorously. N-Boc-3-iodoalanine methyl ester (47.90 g, 0.14 mol) in DMF (50 mL) was added to the reaction mixture, which was then stirred at room temperature for 2 h. The reaction mixture was then standing for another 30 min, the supernatant liquid was transferred to TA-103 (23.0 g, 0.06 mol), Pd(OAc)$_2$ (1.30 g, 5.8 mmol), and S-PHOS (2.38, 5.8 mmol) via syringe. The reaction mixture was stirred at 35° C. for 4 h. After pouring into water, the mixture was extracted with ethyl acetate (2*50 mL). The combined organic layers were washed with brine (2*50 mL), dried over sodium sulfate, and concentrated in vacuo. The residue was purified by silica gel column chromatography (hexane:ethyl acetate=5:1) to give the product TA-104 (16.2 g, 54% yield). $^1$H NMR (400 MHz, CD$_3$OD) δ 8.27 (d, J=8.0 Hz, 1H), 7.88 (d, J=8.0 Hz, 1H), 7.75 (d, J=8.0 Hz, 2H), 7.37 (t, J=8.0 Hz, 1H), 7.26 (m, 3H), 5.00 (d, J=8.0 Hz, 1H), 4.56 (m, 1H), 3.69 (s, 3H), 3.39 (dd, J=15.2, 4.8 Hz, 1H), 3.13 (m, 1H), 2.36 (s, 3H), 1.35 (s, 9H).

2.6. General Procedure for Preparation of Compound TA-105

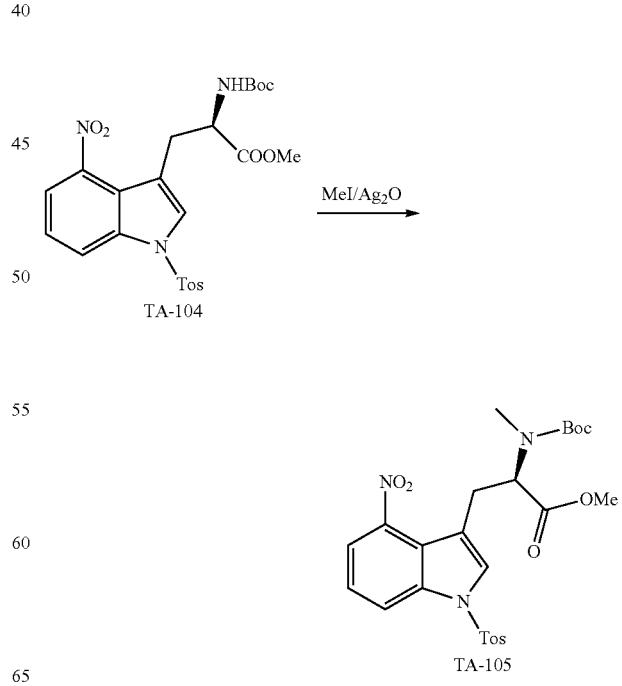

A mixture of TA-104 (16.2 g, 0.03 mol), Ag₂O (51.0 g, 0.2 mol), methyl iodide (100 mL) and DMF (200 mL) was stirred at room temperature for 16 h. The insoluble materials were filtered off and the filtrate was concentrated to dryness to give the crude product TA-105 (17.90 g) which can be used without further purification.

2.7. General Procedure for Preparation of Compound TA-106

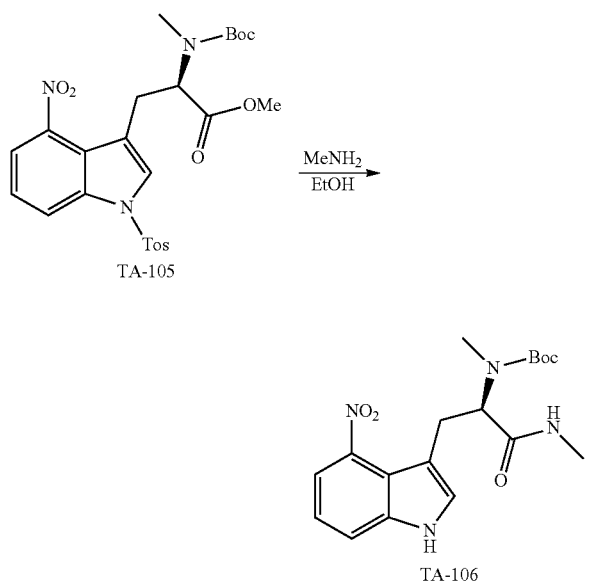

To a solution of TA-105 in EtOH (20 mL) was added dropwise 30% methylamine in EtOH (80 mL) at room temperature and the resulting mixture was stirred for 16 h. The reaction mixture was concentrated to dryness and the residue was used without any further purification.

2.8. General Procedure for Preparation of Compound TA-107

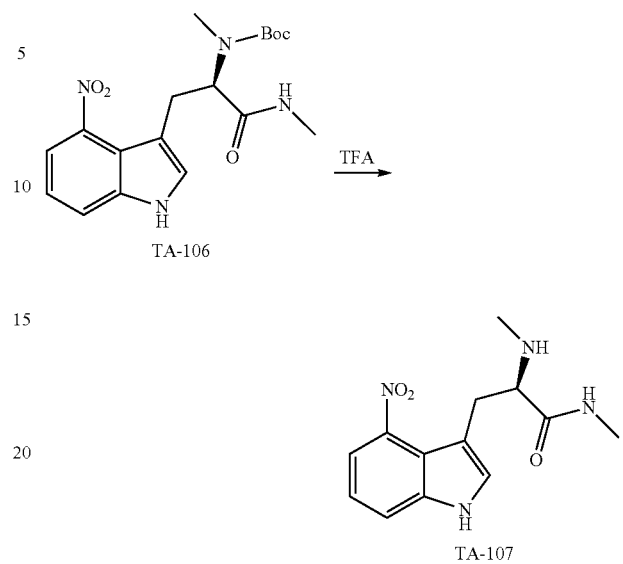

To a solution of TA-106 in DCM (25 mL) was added TFA (15 mL) at 0° C. The mixture was stirred for 0.5 h at room temperature. The reaction mixture was poured into aqueous NaHCO₃ and extracted with DCM (2×25 mL). The extract was washed with water and brine. The solvent was evaporated to dryness and the residue was purified by silica gel column chromatography (DCM:MeOH=20:1, v/v) to give TA-107 (1.65 g, 19% yield over 3 steps). ¹H NMR (400 MHz, CD₃OD) δ 8.02 (d, J=8.0 Hz, 1H), 7.80 (d, J=8.0 Hz, 1H), 7.43 (s, 1H), 7.28 (t, J=8.0 Hz, 1H), 3.93 (m, 1H), 3.65 (dd, J=13.6, 5.2 Hz, 1H), 3.34 (d, J=5.2 Hz, 1H), 2.69 (s, 3H), 2.60 (s, 3H).

2.9. General Procedure for Preparation of TA-108

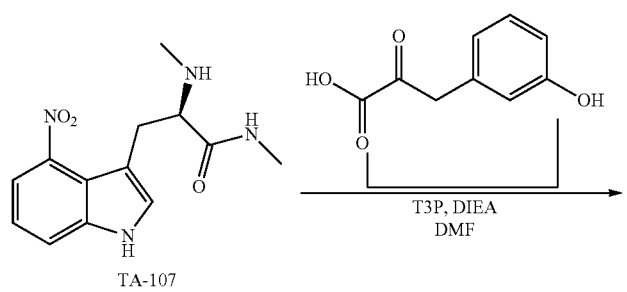

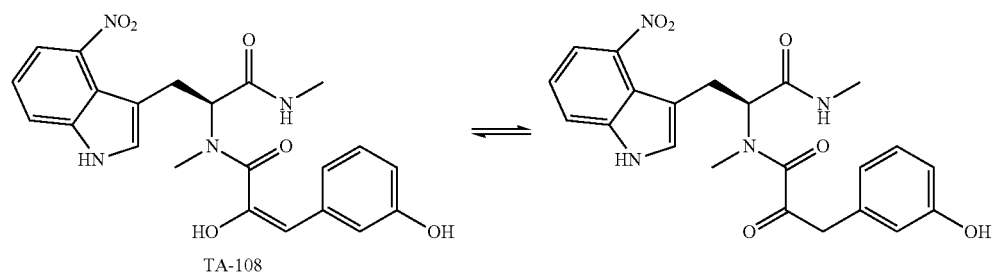

A mixture of TA-107 (1.30 g, 4.7 mmol) and TA-205 (1.30 g, 7.2 mmol) in its keto form and DIEA (1.2 g, 9.3 mmol) in DMF (5 ml) was treated dropwise with a DMF solution containing 50% T3P (6.0 mL) under an Argon atmosphere at 0° C. After 12 hours' stirring at room temperature, the mixture was washed with ice-water, then with saturated NaCl solution. The solvent was evaporated to dryness and the residue was purified by silica gel column chromatography (DCM: MeOH=10:1) to give the product TA-108 (1.6 mg, 78% yield) which can be used directly.

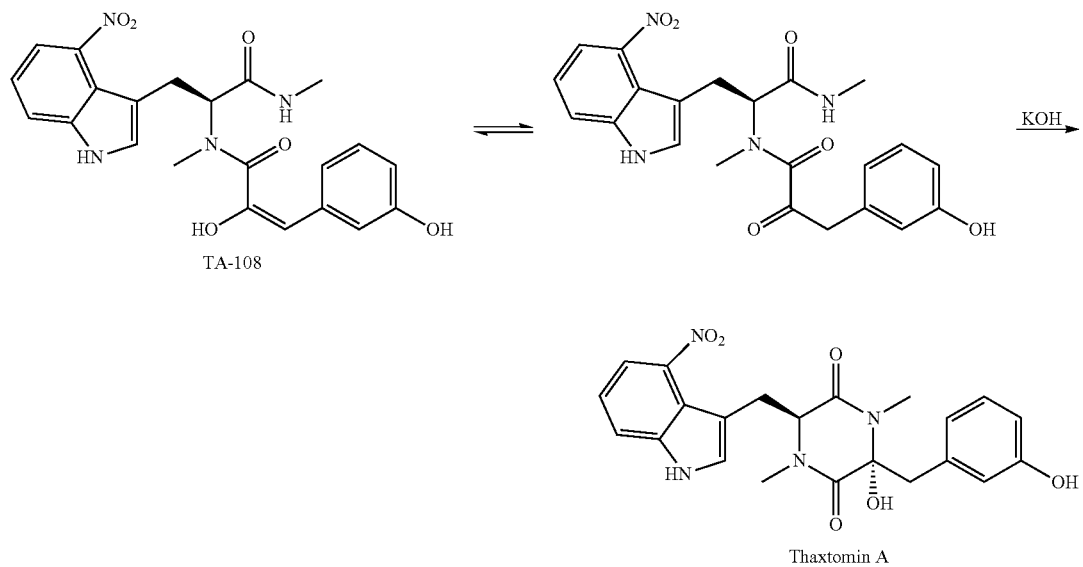

To a solution of TA-108 (1.6 g, 3.6 mmol) in MeOH (4 mL) was added KOH (0.80 g, 14.3 mmol) at room temperature. The mixture was stirred for 12 h at 40° C., then the solvent was removed in vacuo. The residue was poured into ice-water, adjusted with 0.5N HCl to a pH of 6-7 and extracted with ethyl acetate. The extraction was evaporated to dryness and the residue was purified by silica gel column chromatography (DCM:MeOH=100:1) to give the crude product (680 mg). After recrystallizing twice using a mixture of 2 mL MeOH and 10 mL EtOAc the yellow product (±) Thaxtomin A (248 mg) was obtained. Both enantiomers were obtained in high enantiomeric purity by preparative chiral liquid chromatography. $^1$H NMR (400 MHz, CDCl$_3$) δ 7.73 (d, J=8.0 Hz, 1H), 7.59 (d, J=8.0 Hz, 1H), 7.11 (m, 2H), 6.85 (s, 1H), 6.64 (d, J=8.0 Hz, 1H), 6.60 (m, 2H), 3.76 (m, 1H), 3.25 (d, J=13.6 Hz, 1H), 3.02 (d, J=13.6 Hz, 1H), 2.90 (s, 3H), 2.72 (s, 3H), 2.50 (dd, J=14.0, 6.0 Hz, 1H), 1.51 (dd, J=14.0, 8.8 Hz, 1H).

3. Comparison of Herbicidal Activity Between Synthesized and Natural Thaxtomin A Synthesized thaxtomin A and thaxtomin A from fermentation were separately dissolved in ethanol first (final ethanol concentration in the spraying solution was 2%), then added into 0.2% Glycosperse O-20 water solution. Sonication completely dissolved the thaxtomin A. The concentration of thaxtomin A was 0.25 and 1.0 mg/mL. Water with 2% ethanol and 0.2% Glycosperse O-20 was used as a blank control. Fifteen day mustard plants were used in the experiments. Four replicates for each concentration of thaxtomin A were carried out. Spraying was performed using a Track Sprayer. The herbicidal activity was graded as percent control. Herbicidal activity was counted on the $7^{th}$ and $14^{th}$ days, respectively. The comparison of the herbicidal activity for each of the concentrations of each of the thaxtomins is shown in the FIGURE. There is no significant difference of herbicidal activity between the synthetic and natural thaxtomin A The terms and expressions which have been employed are used as terms of description and not of limitation, and there is no intention in the use of such terms and expressions of excluding any equivalents of the features shown and/or described or portions thereof, it being recognized that various modifications are possible within the scope of the invention.

Various references are cited throughout this specification, each of which is incorporated herein by reference in its entirety.

CITED REFERENCES

1. King, R. R., Calhoun, L. A., synthesis and NMR characteristics of N-acetyl-4-nitro, N-acetyl-5-nitro, N-acetyl-6-nitro and N-acetyl-7-nitrotryptophan methyl esters, *Magnetic Resonance in Chemistry,* 2009, 47: 273-276.
2. King, R. R., Lawrence, C. H., Calhoun, L. A., Chemistry of phytotoxins associated with *Streptomyces scabies*, the causal organism of potato common scab, *J. Agric. Food Chem.,* 1992, 40: 834-837.
3. King, R. R., Lawrence, C. H., 4-Nitrotryptophans associated with the in vitro production of thaxtomin A by *Streptomyces scabies, Phytochemistry,* 1995, 40: 41-43.
4. King, R. R., Lawrence, C. H., Embleton, J., Calhoun, L. A., More chemistry of the thaxtomin phytotoxins, *Phytochemistry,* 2003, 64: 1091-1096.
5. Johnson, E. G., Krasnoff, S. B., Bignell, D. R. D., Chung, W. C., Tao, T., Parry, R. J., Loria, R., Gibson, D. M., 4-nitrotryptophan is a substrate for the non-ribosomal peptide synthetase TxTB in the thaxtomin A biosynthetic pathway, *Molecular Microbiology,* 2009, 73: 409-418.
6. King, R. R., Calhounb, L. A., The thaxtomin phytotoxins: Sources, synthesis, biosynthesis, biotransformation and biological activity, Phytochemistry 70 (2009) 833-841.

7. King, R. R., Lawrence, C. H., Clark, M. C., Calhoun, L. A., Isolation and Characterization of Phytotoxins Associated with *Streptomyces scabies*, J. CHEM. SOC., CHEM. COMMUN., 1989, 849-850.
8. King, R. R., Lawrence, C. H., Isolation and Characterization of Thaxtomin-Type *Phytotoxins Associated with Streptomyces iponweae*, J. Agric. Food Chem. 1994, 42, 1791-1794.
9. Gelin, J., Mortier, J., Moyroud, J., Synthetic Studies on Thaxtomins A and B, Phytotoxins Associated with *Streptomyces scabies*, the Causal Organism of Potato Common Scab, J. Org. Chem., 1993, 58(13) 3473-3475.
10. King, R. R., Synthesis of Thaxtomin C, Can. J. Chem., 1997, 75, 1172-1173.
11. Molesworth, P. P., Gardiner, M. G., Jones, R. C., Smith, S. J., et al., Synthesis and Phytotoxicity of Structural Analogues of Thaxtomin Natural Products, Aust. J. Chem. 2010, 63, 813-820.
12. Krasnoff, S. B., Lobkovsky, E. B., et al., Chemistry and Phytotoxicity of Thaxtomin A Alkyl Ethers, J. Agric. Food Chem. 2005, 53, 9446-9451.
13. Fellows, H., Relation of growth in the potato tuber to the potato-scab disease. Journal of Agricultural Research, 1926 (8) 757-781.
14. King, R R; Lawrence, C H; Gray, J A, Herbicidal Properties of the thaxtomin Group of phytotoxins, J. Agric. Food Chem, 2001 (59) 2298-2301.
15. Schneegurt, M. A.; Heim, D. R.; LARRINUA, I. M., Investigation into the Mechanism of Isoxaben Tolerance in Dicot Weeds, Weed Science, 1994, 42, 163-167.
16. Scheible, W R; Fry, B; Kochevenko, A; et al. An Arabidopsis mutant resistant to thaxtomin A, a cellulose synthesis inhibitor from *Streptomyces* species, PLANT Cell, 2003, 1781-1794.

What is claimed is:

1. A method for the synthesis of a thaxtomin or analog thereof having the structure (I)

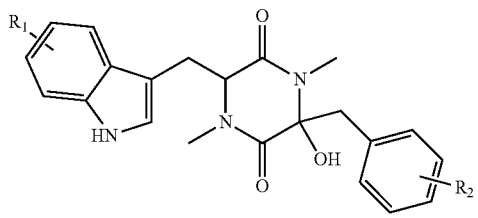

wherein R1 is NO$_2$ and R2 is selected from a lower alkyl, hydroxyl, halogen, fluoromethyl, difluoromethyl, trifluoromethyl, nitro, amine, methoxy, fluoromethoxy, difluoromethoxy, and trifloromethoxy, comprising:

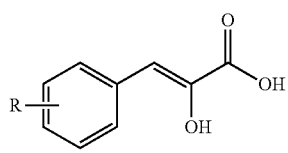

(a) reacting a tryptophan amide analog having the structure

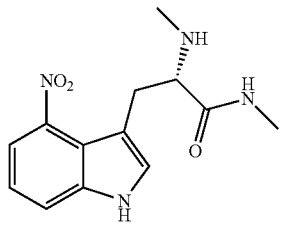

with substituted phenyl acrylic acid having the structure

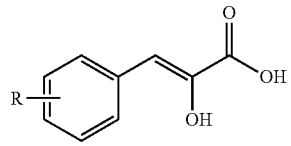

wherein R is selected from a lower alkyl, hydroxyl, halogen, fluoromethyl, difluoromethyl, trifluoromethyl, nitro, amine, methoxy, fluoromethoxy, difluoromethoxy, and trifloromethoxy, or its keto tautomer to obtain a compound having the structure (A2)

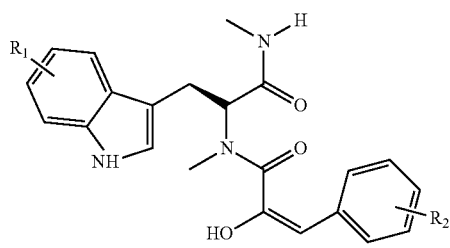

wherein R1 is NO$_2$ and R2 is selected from a lower alkyl, hydroxyl, halogen, fluoromethyl, difluoromethyl, trifluoromethyl, nitro, amine, methoxy, fluoromethoxy, difluoromethoxy, and triflorometoxy; and (b) subjecting the compound having the structure (A2) to a cyclization agent to obtain the structure (I).

2. The method according to claim 1, wherein said thaxtomin analogue is thaxtomin A having the structure

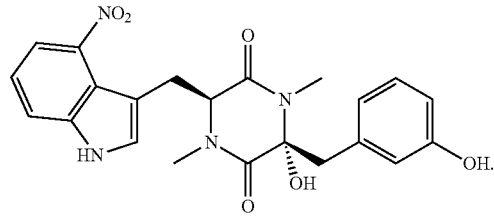 [SMILES: CN1C(=O)[C@](O)(Cc2cccc(O)c2)N(C)C(=O)[C@@H]1Cc1c[nH]c2cccc([N+](=O)[O-])c12]

3. The method according to claim 1, wherein said substituted phenylacrylic acid has the structure

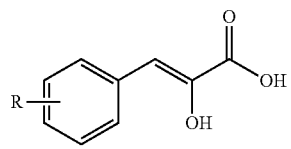

wherein R is OH or its keto tautomer.

4. The method according to claim 3, wherein said substituted phenylacrylic acid has the structure

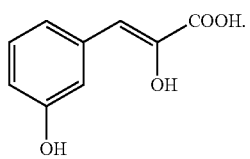 [SMILES: O=C(O)/C(O)=C/c1cccc(O)c1]

5. The method according to claim 1, wherein the cyclization is by means of an organic base.

6. The method according to claim 5 wherein the organic base is potassium hydroxide.

7. The method according to claim 5, wherein the organic base is a chiral Lewis base.

8. The method according to claim 5 wherein the organic base is selected from the group consisting of substituted or unsubstituted pyridine, amine, imidazole, benzimidazole, histidine, and phosphazene.

* * * * *